(12) United States Patent
Looper et al.

(10) Patent No.: US 9,174,021 B2
(45) Date of Patent: Nov. 3, 2015

(54) CATHETER ALLOWING VARIABLE DOSING OF AN ACTIVE AGENT

(75) Inventors: Anthony Looper, Lake Zurich (IL); Griffin Strole, Chicago, IL (US)

(73) Assignee: CAREFUSION 2200, INC., San Diego, CA (US)

( * ) Notice: Subject to any disclaimer, the term of this patent is extended or adjusted under 35 U.S.C. 154(b) by 0 days.

(21) Appl. No.: 13/696,531

(22) PCT Filed: May 6, 2011

(86) PCT No.: PCT/US2011/035533
§ 371 (c)(1),
(2), (4) Date: Jun. 13, 2013

(87) PCT Pub. No.: WO2011/140449
PCT Pub. Date: Nov. 10, 2011

(65) Prior Publication Data
US 2013/0281971 A1    Oct. 24, 2013

Related U.S. Application Data

(60) Provisional application No. 61/332,563, filed on May 7, 2010.

(51) Int. Cl.
*A61M 25/01* (2006.01)
*A61M 25/00* (2006.01)
*A61M 5/168* (2006.01)
*A61M 25/02* (2006.01)

(52) U.S. Cl.
CPC .............. *A61M 25/01* (2013.01); *A61M 25/00* (2013.01); *A61M 5/16877* (2013.01); *A61M 25/007* (2013.01); *A61M 2025/0008* (2013.01); *A61M 2025/0293* (2013.01)

(58) Field of Classification Search
CPC .............................................. A61M 2025/0008
USPC ............................ 604/103.1, 117, 207, 506
See application file for complete search history.

(56) References Cited

U.S. PATENT DOCUMENTS 4,073,321 A * 2/1978 Moskowitz ..................... 141/27
5,487,738 A * 1/1996 Sciulli ............................ 604/414
5,611,778 A * 3/1997 Brinon ........................... 604/117

(Continued)

FOREIGN PATENT DOCUMENTS

CN         101155611 A    4/2008
WO    WO 2009/060322 A2    5/2009

OTHER PUBLICATIONS

May 6, 2014 Office Action issued in Chinese Patent Application No. 201180022943.9.

(Continued)

*Primary Examiner* — Gerald Landry, II
(74) *Attorney, Agent, or Firm* — Arent Fox LLP

(57) ABSTRACT

A drug eluting catheter includes an active agent, such as a drug or chemical substance, which is integrated with the catheter and allows variable dosing of the agent for elution to the patient's body. The catheter includes a dosing region and graduated markings or is associated with a measurement device that includes graduated markings that correspond to a range of dose of the active agent associated with the catheter. By removing or masking an undesired dosing region prior to administration, a user may vary the dosage to suit a patient's needs.

12 Claims, 3 Drawing Sheets

(56) References Cited

U.S. PATENT DOCUMENTS

| | | | |
|---|---|---|---|
| 5,642,730 A | 7/1997 | Baran | |
| 6,287,285 B1* | 9/2001 | Michal et al. | 604/264 |
| 7,469,700 B2 | 12/2008 | Baran | |
| 2004/0019333 A1* | 1/2004 | Graf et al. | 604/207 |
| 2004/0068222 A1* | 4/2004 | Brian | 604/65 |
| 2006/0229573 A1* | 10/2006 | Lamborne | 604/263 |
| 2009/0143633 A1* | 6/2009 | Edmundson et al. | 600/3 |
| 2009/0247983 A1* | 10/2009 | Tremblay et al. | 604/502 |
| 2010/0179513 A1* | 7/2010 | Hebeler, Jr. | 604/529 |
| 2011/0251587 A1* | 10/2011 | Banik et al. | 604/506 |
| 2012/0078226 A1* | 3/2012 | Latere Dwan'Isa et al. | 604/506 |

OTHER PUBLICATIONS

Office Action dated Mar. 27, 2015 issued in Mexican Patent Application No. MX/a/2012/012976 (with English translation).

\* cited by examiner

CATHETER ALLOWING VARIABLE DOSING OF AN ACTIVE AGENT

CROSS-REFERENCE TO RELATED APPLICATION

This application is a National Stage entry of International Application No. PCT/US2011/035533 filed May 6, 2011, which claims priority to U.S. Provisional Patent Application No. 61/332,563 filed May 7, 2010, the disclosure of the prior applications are hereby incorporated in their entirety by reference.

FIELD OF THE INVENTION

The present invention relates to a drug eluting catheter that allows variable dosing of an active agent.

BACKGROUND OF THE INVENTION

Catheters are used in medical procedures and are typically inserted into a patient's body cavity, duct, or vessel. Catheters are typically used to drain fluids, inject fluids, and to provide access for surgical instruments into or from a body cavity. Catheters may allow a user, such as a doctor, nurse, or other medical professional, to access a specific portion of a patient's body without making invasive incisions. Catheters come in a variety of shapes and sizes and may be flexible or rigid, depending on their intended use in a patent's body.

Catheters may also be used to administer agents such as drugs or chemical substances to a specific portion of a patient's body to treat a wide range of medical conditions. These medical conditions include pleural, pulmonary, abdominal, kidney, liver, cardiovascular, digestive, lymphatic, adrenal, thyroid, and other diseases. The agent may be coated on, embedded in, injected through or otherwise applied to the surface of the catheter for elution to the patient's body.

When using a catheter to administer an agent to a patient, a user typically adjusts the dosage of the agent depending on the patient's condition, weight, body mass index (BMI), estimated lung surface area, or other treatments the patient is currently undergoing. In general, higher weight patients require higher doses of agents to treat a medical condition than do patients of lower weight. Some currently available catheters are provided with agents in a range of specified dosages so that a user may select the correct dosage for each patient. Hospitals and other medical facilities must keep in stock a relatively large number of catheters in a wide range of specified dosages, which presents both financial and logistical issues. Other catheters are provided with agents in only one dosage, and do not allow a user to adjust the dosage to account for variations in a patient's weight, BMI, etc.

Thus, there is a need in the art for a drug eluting catheter that allows variable dosing of an agent.

SUMMARY OF THE INVENTION

The present invention provides a drug eluting catheter that includes an active agent, such as a drug or chemical substance that is integrated with the catheter and allows variable dosing of the agent for elution to the patient's body. The catheter is provided with a dosing region and comprises graduated markings, or is associated with a measurement device comprising graduated markings, which correspond to a range of dose of the active agent associated with the catheter. By removing or masking an undesired dosing region prior to administration, a user may vary the dosage to suit a patients needs.

Other novel features and advantages of the present invention will become apparent to those skilled in the art upon examination of the following or upon learning by practice of the invention.

DETAILED DESCRIPTION OF THE INVENTION

Figure 1:
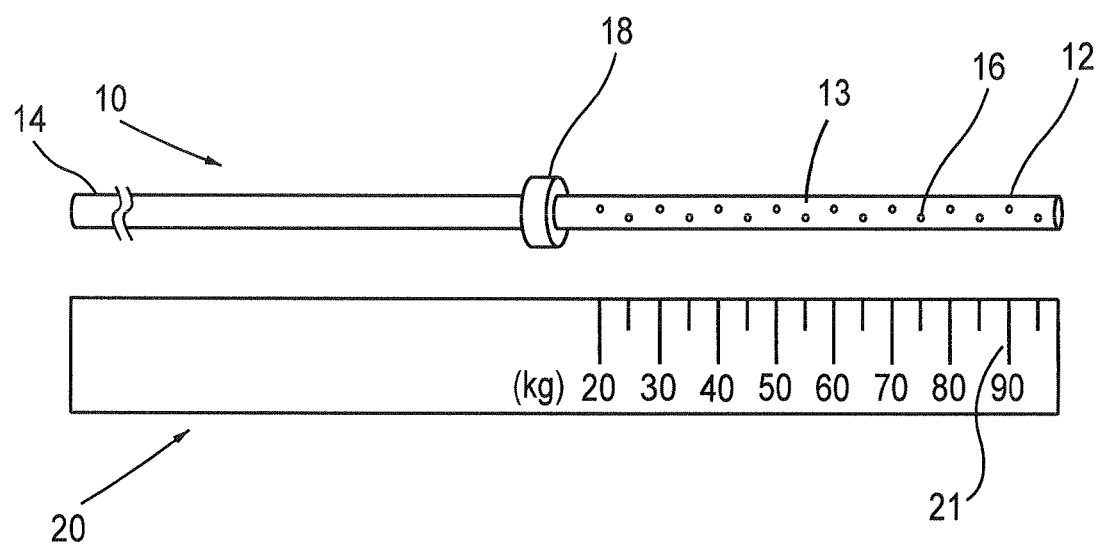
FIG. 1 shows a catheter and a measurement device with graduated markings according to an embodiment of the invention.

The present invention provides a drug eluting catheter that includes an active agent, such as a drug or chemical substance that is integrated with the catheter and allows variable dosing of the agent for elution to the patient's body. The catheter is provided with a dosing region and comprises graduated markings, or is associated with a measurement device comprising graduated markings, which correspond to a range of dose of the active agent associated with the catheter. By removing or masking an undesired dosing region prior to administration, a user may vary the dosage to suit a patient's needs.

The dosing region of the catheter of the present invention includes the active agent. The agent may be coated on, embedded in, or otherwise applied to the dosing region for elution to the patient's body. The agent may be applied to the dosing region by any method known in the art, such as those described in WO 2009/060322 and U.S. Pat. No. 6,287,285, the disclosures of which are fully incorporated herein by reference.

The dosing region may be substantially uniform in concentration of the active agent. Alternatively, the agent may be applied to the dosing region in a specified pattern including, but not limited to, a strip that runs along the dosing region, or in a pattern with varying concentrations that correspond to specific dosages for each graduated marking of the catheter or a measuring device.

The dosing region of the catheter, prior to removal or masking of an undesired dosing region, corresponds to the maximum dosage of the agent. Thus, a user may administer the maximum dosage of the agent to a patient by not removing or masking any portion of the dosing region. Alternatively, the user may administer a smaller dosage of the agent by removing or masking a portion of the dosing region.

The graduated markings correspond to a range of doses of the agent. The graduated markings are spaced at predetermined intervals on a surface of the dosing region of the catheter or on a measurement device, such as a ruler, that is used in association with the catheter. For example, the graduated markings may be positioned at regular intervals along the length of the dosing region or the measurement device.

The graduated markings may include, but are not limited to, one or more of lines, dots, alphanumeric characters, colors, symbols, fenestrations, or any other type of visual marking. For example, graduated lines and numbers corresponding to varying patient weights may be positioned along the length of the catheter. The graduated markings may also be made in a variety of two or more alternating colors to allow a user to easily identify the varying dosages.

The graduated markings may be raised, substantially flat, or scored on the surface of the catheter or on a measurement device that is used in association with the catheter. For example, raised or substantially flat graduated markings may be coated or printed onto the surface of the catheter. A graduated marking that is scored, thereby deforming the surface of the catheter, may allow a user to more easily remove the undesired dosing region.

Any shape, size, or style of catheter that is known in the art may be used in the present invention. The catheter may also be made of any material that is known in the art, as long as it is possible for a user to remove the undesired dosing region to obtain the desired dosage for a patient. For example, the catheter may be made of a polymer, such as silicone, that is inert and unreactive to body fluids and a range of medical fluids with which it may come into contact. The catheter may alternatively include polymers that initiate a biocompatibility reaction and/or inflammatory response when placed in the targeted body cavity, or that dissolve in general or specific body fluids.

The undesired dosing region may be removed by any possible method including, but not limited to cutting, tearing, abrasion, and other physical methods. Other options for removing the undesired dosing region include chemical reaction, and exposure to light and heat. The undesired dosing region may also be masked or covered so that the active agent is not eluted into the patient's body. The masking may be achieved by any possible method, including, but not limited to a sheath, a coating, tape, etc.

The catheter of the invention may optionally include fenestrations. The fenestrations may be used to allow fluid from a patient's body cavity to pass through them, thereby removing the fluid from the cavity. The fenestrations may also be involved in the physical irritation of the patient's body tissues, which is desired in certain medical procedures. For example, the fenestrations may be used to irritate the mesothelial cells that line the visceral and parietal pleurae to achieve pleurodesis. The size of the fenestrations may vary, but they are typically of a size sufficient to allow bodily fluids to pass through them without clogging. The fenestrations may be arranged randomly or in a specified pattern.

The catheter may also include one or more cuffs that assist in positioning the catheter in a patient's body cavity and in surrounding tissues and may reduce the occurrence of infection by creating a seal that prevents external microorganisms from penetrating and infecting the body cavity. The cuffs may be made of any suitable material that is commonly used in catheters including, but not limited to, polyester.

According to an embodiment of the invention, the catheter includes a dosing region that includes an active agent. The catheter is associated with a measurement device that is separate from the catheter. The measurement device, which may be linear in form, such as a ruler, has graduated markings that correspond to a range of dosages of the agent. The measurement device may be made of any material, such as a plastic, that may be coated or printed with graduated markings, as discussed above.

To vary the dosage of the agent, a user aligns the measurement device with the dosing region by positioning an end of the measurement device against the dosing region. Using the graduated markings, the user may remove or mask the undesired dosing region to obtain the accurate dosage for a patient.

An example of a catheter and measurement device according to this embodiment of the invention is shown in FIG. 1. The catheter 10 includes a distal end 12 and a proximal end 14. A dosing region 13 including an active agent is positioned toward the distal end 12. The proximal end 14 may be joined to a drainage container or other medical device. The catheter 10 may include a cuff 18 and fenestrations 16 that are positioned between the distal end 12 of the catheter 10 and the cuff 18.

The catheter 10 is associated with a measurement device 20 having graduated markings 21 that correspond to a range of dosages of the agent. As shown in FIG. 1, graduated markings 21 may include lines and numbers corresponding to a range of patient weights that are positioned along the measurement device 20. The graduated markings 21 allow a user to easily determine the proper dosage and remove or mask the undesired dosing region 13 to obtain the accurate dosage for a patient.

According to another embodiment of the invention, the catheter includes a dosing region that includes an active agent and includes fenestrations. The fenestrations are arranged in a specified pattern, such as at regular intervals along the length of the catheter. In this embodiment, the fenestrations serve as graduated markings that denote the range of doses of the agent. The catheter may also include numbers or other symbols corresponding to varying patient weights that are positioned along the dosing region. In use, a user removes or masks the undesired dosing region, as indicated by the position of the fenestrations or other graduated markings, to obtain a desired dosage for a patient.

Figure 2:
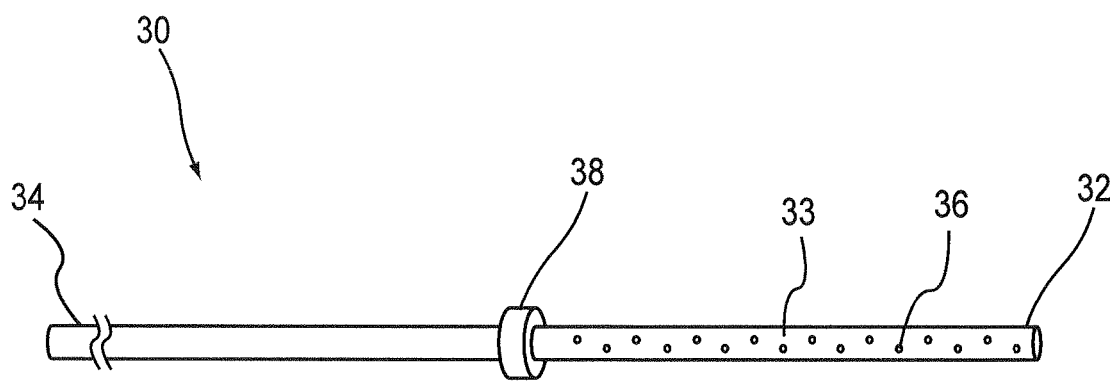
FIG. 2 shows a catheter with graduated fenestrations according to another embodiment of the invention.

An example of a catheter according to this embodiment of the invention is shown in FIG. 2. The catheter 30 includes a distal end 32 and a proximal end 34. A dosing region 33 including an agent is positioned toward the distal end 32. The catheter 30 may include a cuff 38. The catheter 30 includes fenestrations 36 that are positioned between the distal end 32 of the catheter 30 and the cuff 38. As shown in FIG. 2, the fenestrations 36 are arranged at regular intervals along the length of the dosing region 33.

According to another embodiment of the invention, the catheter may include a dosing region that includes an active agent and graduated markings that are arranged at regular intervals along the dosing region. The graduated markings denote the range of doses of the agent. The catheter may include additional graduated markings, such as numbers corresponding to varying patient weights that are positioned along the dosing region. The catheter may optionally include fenestrations, but they are not required in applications where fluid is not being removed from a body cavity. In use, a user removes or masks the undesired dosing region, as indicated by the position of the graduated markings, to obtain a desired dosage for a patient.

Figure 3:
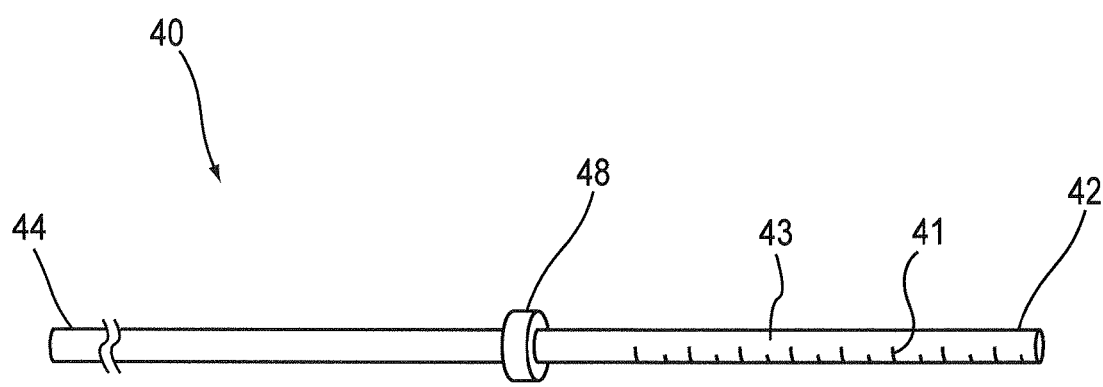
FIG. 3 shows a catheter with graduated markings according to another embodiment of the invention.

An example of a catheter according to this embodiment of the invention is shown in FIG. 3. The catheter 40 includes a distal end 42 and a proximal end 44. A dosing region 43 including an agent is positioned toward the distal end 42. The catheter 40 may include a cuff 48. The catheter 40 includes graduated markings 41 that are positioned between the distal end 42 of the catheter 40 and the cuff 48 and denote the range of doses of the agent. As shown in FIG. 3, the graduated markings 41 are arranged at regular intervals along the length dosing region 43.

A catheter according to the present invention may be used to treat a wide range of medical conditions. For example, a catheter according to the present invention may be used to administer sclerosing agents during a pleurodesis procedure to treat pleural diseases such as pleural effusions and pneumothorax. Pleural effusions involve the build-up of fluid around the lungs and can be associated with conditions such as cancer, tuberculosis, congestive heart failure, pneumonia, pulmonary emboli, cirrhosis, pancreatitis, and collagen vascular diseases. Pneumothorax occurs when air or gas is present in the pleural cavity.

Patients with pleural effusions or pneumothorax are typically treated with thoracentesis to remove fluid or air, and/or chemical or mechanical pleurodesis. Pleurodesis involves irritation of the parietal and/or visceral layers of the pleura to adhere them together and thus eliminate the pleural space, preventing further fluid and/or air accumulation. Pleurodesis is typically characterized by the creation of fibrous adhesions between the parietal and visceral layers of the pleura. Chemical pleurodesis can be achieved with the insertion of sclerosing agents, typically by catheter, into the pleural space. Sclerosing agents may include, but are not limited to, talc, tetracycline, doxycycline, minocycline, doxorubicin, povidone iodine, bleomycin, TGFβ, and silver nitrate.

To administer a sclerosing agent using a catheter according to the present invention, the catheter is coated or embedded with a sclerosing agent.

The dosages of active agents vary depending on the agent, which are well-known. Possible agents and their dosages are described in "Pleural Diseases", $5^{th}$ Edition, Richard W. Light (2007 Lippincott Williams & Wilkins), and "Textbook of Pleural Diseases", $2^{nd}$ Edition, Richard W. Light and Y. C. Gary Lee, (2008 Hodder Arnold), the disclosures of which are fully incorporated herein by reference. Typical doses may be about 2,500 mg to about 10,000 mg for talc, about 250 mg to about 1,000 mg for doxycycline, about 25 mg to about 100 for bleomycin, about 100 mg to about 400 for silver nitrate, and about 1,000 mg to about 4,000 mg for povidone iodine.

The catheter of the present invention may include any combination of the features described above.

The invention claimed is:

1. A catheter system comprising:
    a catheter comprising a dosing region; and
    an active agent coated or embedded at the dosing region; and
    a measurement device having graduated markings, wherein the graduated markings are indicative of a dosage of the active agent.

2. The catheter system of claim 1, wherein the graduated markings are selected from the group consisting of lines, dots, alphanumeric characters, symbols, and fenestrations.

3. The catheter system of claim 1, wherein the graduated markings include one or more colors.

4. A catheter comprising:
    a dosing region;
    an active agent coated or embedded at the dosing region; and
    graduated markings disposed at the dosing region, wherein the graduated markings are indicative of a dosage of the active agent.

5. A method of administering an agent to a patient comprising:
    providing a catheter comprising:
        a dosing region; and
        an agent coated or embedded at the dosing region;
    providing a measurement device comprising graduated markings, wherein the graduated markings are indicative of a dosage of the agent; and
    removing or masking a portion of the dosing region corresponding to a specific dosage of the agent.

6. A method of varying a dosage of an active agent comprising:
    providing a catheter comprising:
        a dosing region; and
        an agent coated or embedded at the dosing region;
    providing a measurement device comprising graduated markings, wherein each of the graduated markings is indicative of a different dosage of the active agent; and
    removing or masking a portion of the dosing region corresponding to a specific dosage of the active agent.

7. A method of administering an agent to a patient comprising:
    providing a catheter comprising:
        a dosing region;
        an agent coated or embedded at the dosing region; and
        graduated markings disposed at the dosing region, wherein each of the graduated markings is indicative of a different dosage of the active agent; and
    removing Or masking a portion of the dosing region corresponding to a specific dosage of the active agent.

8. A method of varying a dosage of an agent comprising:
    providing a catheter comprising:
        a dosing region;
        an agent coated or embedded at the dosing region; and
        graduated markings disposed at the dosing region, wherein each of the graduated markings is indicative of an incremental dosage of the active agent; and
    removing or masking a portion of the dosing region corresponding to a dosage of the active agent required for treating a patient having a particular weight.

9. The catheter system of claim 1, wherein the active agent is a sclerosing agent.

10. The catheter system of claim 9, wherein the sclerosing agent is selected from a group consisting of talc, tetracycline, doxycycline, minocycline, doxorubicin, providone iodine, bleomycin, TGFβ and silver nitrate.

11. The catheter system of claim 5, wherein the active agent is a sclerosing agent.

12. The catheter system of claim 11, wherein the sclerosing agent is selected from a group consisting of talc, tetracycline, doxycycline, minocycline, doxorubicin, providone iodine, bleomycin, TGFβ and silver nitrate.

* * * * *